United States Patent
Lindell et al.

(10) Patent No.: US 9,879,288 B2
(45) Date of Patent: Jan. 30, 2018

(54) USE OF MARINE ALGAE FOR PRODUCING POLYMERS

(75) Inventors: Scott R. Lindell, Falmouth, MA (US); Christopher M. Reddy, Falmouth, MA (US); Gregory W. O'Neil, Bellingham, WA (US)

(73) Assignees: Woods Hole Oceanographic Institution, Woods Hole, MA (US); Marine Biological Laboratory, Woods Hole, MA (US); Western Washington University, Bellingham, WA (US)

(*) Notice: Subject to any disclaimer, the term of this patent is extended or adjusted under 35 U.S.C. 154(b) by 654 days.

(21) Appl. No.: 13/298,576

(22) Filed: Nov. 17, 2011

(65) Prior Publication Data

US 2012/0165490 A1 Jun. 28, 2012

Related U.S. Application Data

(60) Provisional application No. 61/414,491, filed on Nov. 17, 2010.

(51) Int. Cl.
| | |
|---|---|
| C12P 5/02 | (2006.01) |
| C12P 7/26 | (2006.01) |
| C12N 1/12 | (2006.01) |
| C12P 7/64 | (2006.01) |

(52) U.S. Cl.
CPC .............. *C12P 7/26* (2013.01); *C12N 1/12* (2013.01); *C12P 7/649* (2013.01); *C12P 5/026* (2013.01); *Y02E 50/13* (2013.01)

(58) Field of Classification Search
CPC ............... C12N 1/26; C12P 1/00; C12P 5/026
USPC ....... 424/283.1, 780; 435/47, 71.1, 134, 166
See application file for complete search history.

(56) References Cited

U.S. PATENT DOCUMENTS

| | | | |
|---|---|---|---|
| 5,770,043 A | 6/1998 | Ellis et al. | |
| 7,368,200 B2* | 5/2008 | Zhu et al. | 429/494 |
| 7,476,705 B2* | 1/2009 | Pajerski | 524/591 |
| 2005/0192388 A1* | 9/2005 | Craun | C08K 5/10 524/284 |
| 2010/0170144 A1* | 7/2010 | Day | C12P 7/6418 44/388 |
| 2011/0167714 A1 | 7/2011 | Lindell et al. | |

FOREIGN PATENT DOCUMENTS

| | | |
|---|---|---|
| CN | 101368193 A | 2/2009 |
| ES | 2088366 A1 | 8/1996 |
| WO | WO-2008/079724 A2 | 7/2008 |
| WO | WO-2009/018230 A1 | 2/2009 |

OTHER PUBLICATIONS

U.S. Appl. No. 14/187,929.*
Christi, Yusuf, 'Biodiesel from microalgae', Biotechnology Advances, vol. 25, available online Feb. 13, 2007, pp. 294-306. Retrieved from the Internet on Mar. 3, 2011: <http://linkinghub:elsevier.com/pii/s0734975007000262. see pp. 294-304>.
International Search Report PCT/US2010/060259.
Eltgroth, M.L., et al., "Production and cellular localization of long-chain neutral lipids in the haptophyte algae *Isochrysis galbana* and *Emiliania huxleyi*" J. Phycol, 2005, 41, 1000-1009.
Goepfert, Tyler Jay, 'Microbial Biofuels: *Isochrysis* sp. and *Phaedactylum tricornium* lipid characterization and physiology studies' (Thesis paper), Carl von Ossietzky University, Oldenberg, Germany, Mar. 15, 2010. Retrieved from the Internet on Mar. 3, 2011; <http://www.whoi.edu/cms/files/Goepfert_MasterThesis_60365.pdf>.
Haiduc, et al., "An integrated process for hydrothermal production of methane from microalgae and CO 2 mitigation" J. Appl. Phycol., 2009, 21:529-541.
Stucki, et al., "Catalytic gasification of algae in supercritical water for biofuel production and carbon capture" Energy Environ. Sci., 2009, 2:535-541.
Versteegh, G.J.M., et al., 'Uk'37 values for *Isochrysis galbana* as a function of culture temperature, light intensity and nutrient concentrations' Organic Geochemistry, 2001, 32, 785-794.
O'Neil et al., "Beyond Fatty Acid Methyl Esters: Expanding the Renewable Carbon Profile with Alkenones from *Isochrysis* sp.," Energy Fuels, 26:2434-2441 (2012).

* cited by examiner

*Primary Examiner* — Ruth Davis
(74) *Attorney, Agent, or Firm* — Melissa Hunter-Ensor; Leslie Serunian; Greenberg Traurig, LLP

(57) ABSTRACT

In certain aspects, the disclosure provides methods for producing polymers from alkenone-producing algae, such as algae species of the Isochrysis family.

16 Claims, 2 Drawing Sheets

USE OF MARINE ALGAE FOR PRODUCING POLYMERS

PRIORITY

This application claims the benefit of U.S. Provisional Application No. 61/414,491, filed on Nov. 17, 2010, the disclosure of which is incorporated herein by reference in its entirety.

BACKGROUND

The broad class of polymeric materials includes polymers with excellent processability, chemical resistance, and mechanical properties. These properties allow polymers to be used to produce extrusion molded articles, injection molded articles, hollow molded articles, films, sheets and the like, in a wide variety of industries. Numerous polymers are derived from petroleum and natural gas. Market prices for these fossil fuels are increasing, due to a number of factors including a depletion of easily accessible deposits, growth of emerging economies, political instabilities, and environmental concerns. There is an unmet need in the art for polymer production methods that do not rely on fossil fuels.

SUMMARY OF THE INVENTION

In accordance with the present invention, methods are provided for producing polymers from algae. In one aspect, the disclosure provides a method which comprises: (a) culturing an alkenone-producing alga under a growth condition sufficient to produce alkenones within the alga; (b) optionally chemically modifying the alkenones to produce alkenone derivatives, and (c) polymerizing the alkenones or alkenone derivatives. In certain embodiments, the alkenone-producing alga is a species of the Isochrysis family, such as *Isochrysis galbana, Isochrysis* sp. T-Iso, and *Isochrysis* sp. C-Iso. The alkenones of the alga may comprise alkenones having a number of carbons ranging from 35 to 40. The alkenones may be converted to hydrocarbons by catalytic hydroprocessing. In certain embodiments, the alkenones are processed into a liquid fuel such as diesel and gasoline. In other embodiments, the alkenones are processed into a gaseous fuel, such as a syngas (a mixture of CO and $H_2$) and/or a synthetic hydrocarbon gas (e.g., methane, propane, and butane). In certain embodiments, the alga also produces fatty acid methyl esters (FAMEs). Optionally, the method comprises converting a mixture of FAMEs and alkenones to hydrocarbons without separating the FAMEs from the alkenones. In certain embodiments, the growth condition for culturing the alga may include a stationary growth phase, a high temperature, sufficient light, nutrient limitation or a combination thereof. In certain specific embodiments, algae are directly converted into methane via hydrothermal gasification. Optionally, growing of algae and hydrothermal processing of algae biomass are coupled into a continuous process.

In certain embodiments, chemically modifying the alkenones comprises pyrolyzing or cracking the alkenones. In some embodiments, alkenone derivatives of step (b) are acrylic acids, acrylic esters, alkenes, vinyl chloride, vinyl acetate, diacids, diamines, diols, or lactic acid.

In certain aspects, the disclosure provides a polymer produced by the claimed methods.

DETAILED DESCRIPTION OF THE INVENTION

Figure 1:
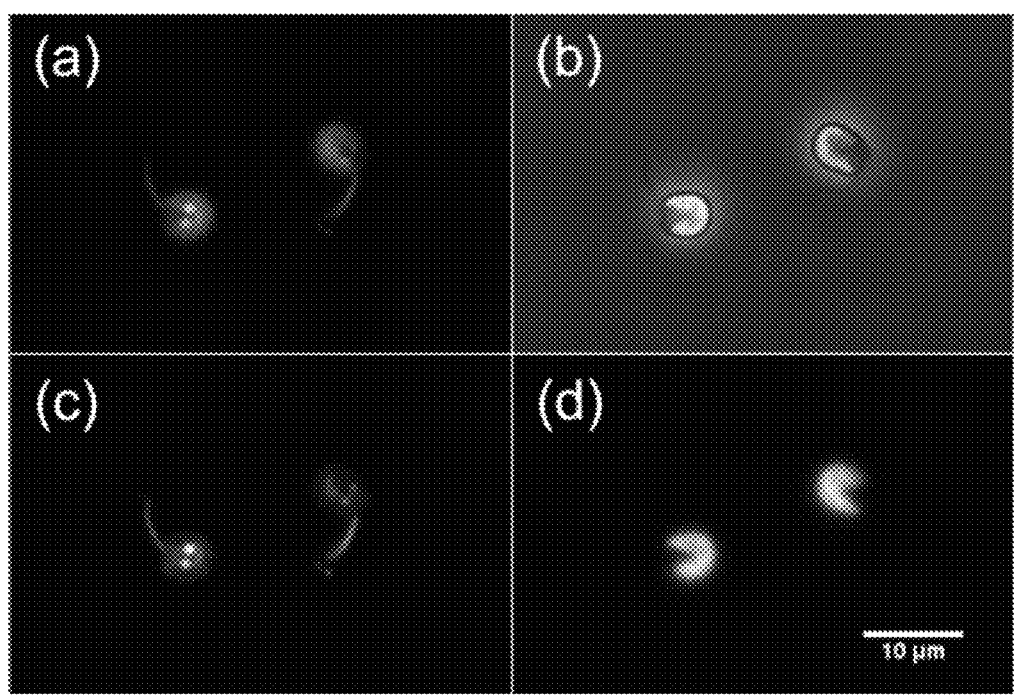
FIGS. 1 (*a*) through (*d*) show *Isochrysis* sp. (T-Iso) micrographs. (*a*) merge of c and d; (*b*) phase contrast image; (*c*) Nile Red stained image with 46HE filter (Ex: 500/25, em: 535/30); and (*d*) chlorophyll autofluoresence through filterset 50 (ex: BP640/30, em: BP690/50). All images were acquired with Zeiss Plan-Neofluar 40×/0.75 Ph2 objective lens and Zeiss Axiocam MRm monochrome camera.
Figure 2:
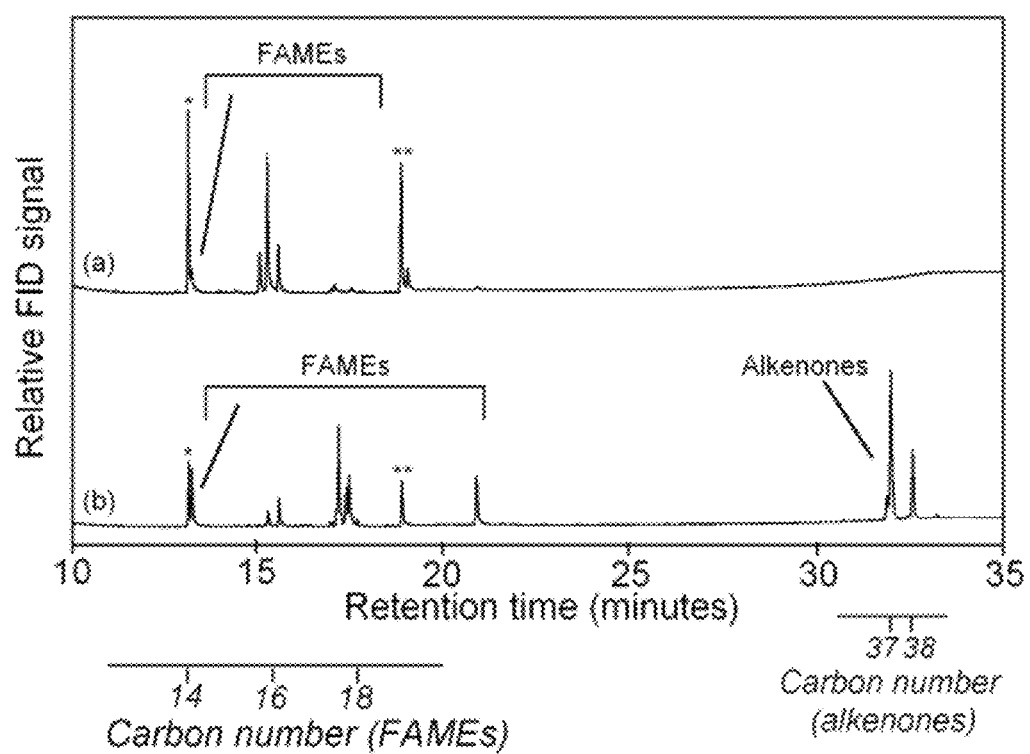
FIGS. 2 (*a*) and (*b*) show gas chromatograms of FAMEs and alkenones extracted from marine algae. (*a*) marine algae *Thalasiosira weissflogii*; and (*b*) *Isochrysis* sp. Note the absence of alkenones in the diatom (*a*). The peaks labeled with "*" and "**" are n-heptadecane and methyl nonadecanoate, used as standards. The FAMEs and alkenones are highlighted in the chromatograms and their respective number of carbons is labeled along the x-axis.

As described below, Applicants found that certain algae species of the Isochrysis family produce polyunsaturated long-chain alkenones, part of a group of compounds including alkenes and alkenoates collectively referred to PULCA. Two common alkenone structures produced by *Isochrysis* sp. are shown below, exemplifying very long carbon chain and the trans-double bonds. Studies have detected methyl and ethyl alkenones with 35 to 40 carbons with two to four double bonds. Nomenclature for alkenones is similar to FAMEs (fatty acid methyl esters); # of carbons: # of double bonds.

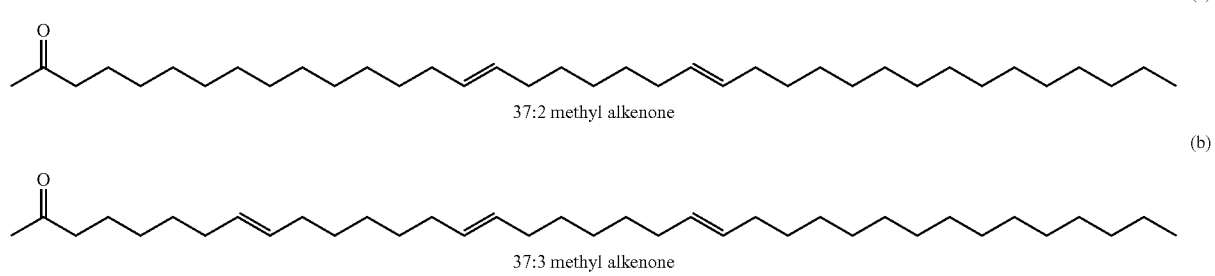

(a) 37:2 methyl alkenone (b) 37:3 methyl alkenone

In certain aspects, the disclosure provides methods for producing hydrocarbons from alkenone-producing algae. In other aspects, the disclosure provides biofuels (e.g., a liquid biofuel or a gaseous biofuel) produced by the subject methods. As used herein, the term "biofuels" refers to any fuel, fuel additive, aromatic, and/or aliphatic compound derived from a biomass starting material (e.g., algae).

In one embodiment, the disclosure provides a method which comprises: (a) culturing an alkenone-producing alga under a growth condition sufficient to produce alkenones within the alga; and (b) converting the alkenones to hydrocarbons. In certain embodiments, the alkenone-producing alga is a species of the Isochrysis family, such as *Isochrysis galbana*, *Isochrysis* sp. T-Iso, and *Isochrysis* sp. C-Iso. The alkenones of the alga may comprise alkenones having a number of carbons ranging from 35 to 40. The alkenones may be converted to hydrocarbons by catalytic hydroprocessing. In certain embodiments, the alkenones are processed into a liquid fuel such as diesel and gasoline. In other embodiments, the alkenones are processed into a gaseous fuel, such as a syngas (a mixture of CO and $H_2$) and/or a synthetic hydrocarbon gas (e.g., methane, propane, and butane). In certain embodiments, the alga also produces fatty acid methyl esters (FAMEs). Optionally, the method comprises converting a mixture of FAMEs and alkenones to hydrocarbons without separating the FAMEs from the alkenones.

While this field is rapidly changing, the majority of biofuels produced at bioproduction facilities are typically mixtures of fatty acid methyl esters (FAMEs) known as biodiesel. This substitute for fossil-fuel diesel is produced from reactions between methanol and glycerides; the latter are the major components of oil and cell membranes in algae as well as terrestrial plants. Biodiesel is used to formulate a range of mixtures from B2 (2% biodiesel mixed with 98% fossil diesel) to B100 (100% biodiesel). More recent technologies are using catalytic hydroprocessing of glycerides to produce "green diesel".

In certain embodiments, the growth condition for culturing the alga may include a stationary growth phase, a high temperature, sufficient light, nutrient limitation, or a combination thereof.

Algae Species as a Hydrocarbon and Feedstock Source

Algae can produce 10 to 100 times as much mass as terrestrial plants in a year. Algae also produce oils (lipids) and starches that may be converted into biofuels. Algae useful for biofuel production include algae known as microalgae, consisting of small, often unicellular, types. These algae can grow almost anywhere, though are most commonly found at latitudes between 40 N and 40S. With more than 100,000 known species of diatoms (a type of algae), 40,000 known species of green plant-like algae, and smaller numbers of other algae species, algae will grow rapidly in nearly any environment, with almost any kind of water, including marginal areas with limited or poor quality water.

Algae can store energy in the form of either oil or starch. Stored oil can be as much as 60% of the weight of the algae. Certain species which are highly prolific in oil or starch production have been identified, and growing conditions have been tested. Processes for extracting and converting these materials to fuels have also been developed. As referred herein, the terms "lipids" and "oil" are used interchangeably.

In certain embodiments, the subject methods make use of certain species of algae which are capable of producing lipids. In a specific embodiment, the subject methods employ algae species which produce alkenones. Polyunsaturated long-chain alkenones, along with alkenes and alkenoates, are collectively referred to as PULCA. These PULCAs typically comprise 35 to 40 carbons methyl or ethyl ketones, although 37 and 38 carbons are generally the most dominant. Certain algae species (e.g., *Isochrysis galbana*, *Emiliania huxleyi* and *Gephyrocapsa oceanica*) produce PULCA and package them into cytoplasmic vesicles or lipid bodies. The amount of these lipid bodies may change in response to various growth conditions. For example, these lipid bodies may increase under nutrient limitation, stationary phase, or high temperatures. On the other hand, these lipid bodies may decrease under prolonged darkness or low temperatures.

Lipid-producing algae can include a wide variety of algae. The most common lipid-producing algae can generally include, or consist essentially of, the diatoms (bacillariophytes), green algae (chlorophytes), blue-green algae (cyanophytes), and golden-brown algae (chrysophytes). In addition, a fifth group known as haptophytes may be used. Specific non-limiting examples of bacillariophytes capable of lipid production include the genera *Amphipleura*, *Amphora*, *Chaetoceros*, *Cyclotella*, *Cymbella*, *Fragilaria*, *Hantzschia*, *Navicula*, *Nitzschia*, *Phaeodactylum*, and *Thalassiosira*. Specific non-limiting examples of chlorophytes capable of lipid production include *Ankistrodesmus*, *Botryococcus*, *Chlorella*, *Chlorococcum*, *Dunaliella*, *Monoraphidium*, *Oocystis*, *Scenedesmus*, and *Tetraselmis*. In one aspect, the chlorophytes can be *Chlorella* or *Dunaliella*. Specific non-limiting examples of cyanophytes capable of lipid production include *Oscillatoria* and *Synechococcus*. A specific example of chrysophytes capable of lipid production includes *Boekelovia*. Specific non-limiting examples of haptophytes include *Isochrysis* and *Pleurochrysis*.

In preferred embodiments, the subject methods employ an alkenone-producing alga, for example, a species of the Isochrysis family which includes, but not limited to, *Isochrysis galbana*, *Isochrysis* sp. T-Iso, and *Isochrysis* sp. C-Iso. Other examples of alkenone-producing algae include *Emiliania huxleyi* and *Gephyrocapsa oceanica*.

In certain aspects, the lipid-producing algae (e.g., alkenone-producing algae) can have lipid content greater than about 20%, and preferably greater than about 30% by weight of the algae. Currently known species contain a practical maximum lipid content of about 40% by weight, although levels as high as 60% have been shown, and strains developed or discovered in the future may achieve practical maximums higher than 40%. Such species would certainly be useful in connection with the present invention. In some embodiments, the lipid-producing algae can comprise lipid content greater than 50%, 60%, 70%, 80%, or 90% by weight of the algae.

In a specific embodiment, the subject methods involve selection of algae species which produce high levels of alkenones. For example, the content of alkenones is at least 20%, 30%, 40%, 50%, 60%, 70%, 80%, or 90% by weight of the algae.

In certain aspects, the subject methods may include a combination of an effective amount of two or more algae species in order to maximize benefits (e.g., achieving optimal production of lipids including alkenones).

In other aspects, the subject methods intend to use a particular algae species, while foreign species are preferably minimized and kept below an amount which would detrimentally affect yields of desired lipids (e.g., alkenones). Undesirable algae species can be controlled and/or eliminated using any number of techniques. For example, careful control of the growth environment can reduce introduction of foreign species. Alternatively, or in addition to other techniques, a virus selectively chosen to specifically target only the foreign species can be introduced into the growth reservoirs in an amount which is effective to reduce and/or eliminate the foreign species. An appropriate virus can be readily identified using conventional techniques. For example, a sample of the foreign algae will most often include small amounts of a virus which targets the foreign algae. This virus can be isolated and grown in order to produce amounts which would effectively control or eliminate the foreign algae population among the more desirable oil-producing algae.

Culturing Algae

In accordance with the present invention, the algae can be grown in reservoir structures, such as ponds, troughs, or tubes, which are protected from the external environment and have controlled temperatures, atmospheres, and other conditions. Optionally, algae growth reservoirs can include a carbon dioxide source and a circulating mechanism configured to circulate lipid-producing algae within the algae growth reservoirs. One way to achieve large surface growth areas is in large ponds or in a captive marine environment. In one embodiment, a raceway pond can be used as an algae growth reservoir in which the algae is grown in shallow circulating ponds with constant movement around the raceway and constant extraction or skimming off of mature algae. Other examples of growth environments or reservoirs include bioreactors.

It is also known that certain species of algae are much more prolific in the production of lipids than others. However, these species may be susceptible to predation or displacement by native or volunteer species which exist naturally in the environment where the growth reservoir is located. Moreover, in most locations, temperatures may reach extremes of heat or cold which could damage or at least retard the growth of the algae. As such, some form of protection is usually desirable for the chosen algae species. In certain embodiments, low-cost greenhouses can be built over the raceway ponds. These greenhouses can have enough integrity to maintain a positive pressure with airlocks, filtration, and temperature control. This integrity can prevent the entrance of wild algae and can maintain desired conditions for the algae crop.

In certain embodiments, the subject methods contemplate culturing an alkenone-producing alga under a growth condition sufficient to produce alkenones within the alga. Optionally, the growth condition for culturing the alga may include growing the alga in a stationary growth phase, growing the alga under a high temperature, growing the alga in the presence of sufficient light (e.g., sunlight), growing the alga under a stress, or a combination thereof. Non-limiting examples of suitable stress include nutrient deprivation (e.g., nitrogen and/or phosphorous), injection of a reactive oxygen source (e.g., ozone or peroxide), and/or chemical additives. The underlying theory is that the algae, under stress, store up energy in the compact form of lipids by extracting carbon and energy from the available nutrients, in preparation for possible long-term harsh conditions (M. L. Eltgroth, et al., J. Phycol, 2005, 41, 1000-1009; G. J. M. Versteegh, et al., Organic Geochemistry, 2001, 32, 785-794).

Recovery of Lipids from the Algae

In certain embodiments, the subject methods relate to recovery of lipids from the algae. Algae store lipids inside the cell body, sometimes but not always in vesicles. The lipids can be recovered in various ways, including solvents, heat, pressure, and/or depolymerizing (such as biologically breaking the walls of the algal cell and/or oil vesicles), if present, to release the lipids from the algae. In certain embodiments, at least one of three types of biological agents may be used to release algae energy stores, for example, enzymes such as cellulase or glycoproteinase, structured enzyme arrays or system such as a cellulosome, a viral agent, or a combination thereof. A cellulase is an enzyme that breaks down cellulose, especially in the wall structures, and a cellulosome is an array or sequence of enzymes or cellulases which is more effective and faster than a single enzyme or cellulase. In both cases, the enzymes break down the cell wall and/or lipid vesicles and release lipids from the cell. Cellulases used for this purpose may be derived from fungi, bacteria, or yeast. Non-limiting examples of each include cellulase produced by fungus *Trichoderma reesei* and many genetic variations of this fungus, cellulase produced by bacteria genus *Cellulomonas*, and cellulase produced by yeast genus *Trichosporon*. A glycoproteinase provides the same function as a cellulase, but is more effective on the cell walls of microalgae, many of which have a structure more dependent on glycoproteins than cellulose.

In addition, a large number of viruses exist which invade and rupture algae cells, and can thereby release the contents of the cell, in particular stored lipids. Such viruses are an integral part of the algal ecosystem, and many of the viruses are specific to a single type of algae. Specific examples of such viruses include the *chlorella* virus PBCV-1 (*Paramecium Bursaria Chlorella* Virus) which is specific to certain *Chlorella* algae, and cyanophages such as SM-1, P-60, and AS-1 specific to the blue-green algae *Synechococcus*. The particular virus selected will depend on the particular species of algae to be used in the growth process. One aspect of the present invention is the use of such a virus to rupture the algae so that lipids inside the algae cell wall can be recovered. In another detailed aspect of the present invention, a mixture of biological agents can be used to rupture the algal cell wall and/or lipid vesicles.

Mechanical crushing, for example, an expeller or press, a hexane or butane solvent recovery step, supercritical fluid extraction, or the like can also be useful in extracting the lipids from lipid vesicles of the algae. Alternatively, mechanical approaches can be used in combination with biological agents in order to improve reaction rates and/or separation of materials.

Once the lipids have been released from the algae, it can be recovered or separated from a slurry of algae debris material, e.g., cellular residue, enzyme, by-products, etc. This can be done by sedimentation or centrifugation, with centrifugation generally being faster. Recovered algal lipids can be collected and directed to a conversion process as described in more detail below.

In certain specific embodiments, the alga also produces fatty acid methyl esters (FAMEs). Optionally, the subject methods involve a mixture of FAMEs and alkenones, without separating the FAMEs from the alkenones.

Conversion of Algal Lipids to Hydrocarbons

In certain embodiments, the subject methods relate to converting algal lipids (e.g., alkenones) into hydrocarbons. In a specific embodiment, a mixture of FAMEs and alkenones are converted to hydrocarbons without separating the FAMEs from the alkenones.

One process for converting algal alkenones (alone or mixed with FAMEs) to hydrocarbons is catalytic hydroprocessing, or cracking Catalytic hydroprocessing technology is well known in the art of petroleum refining and generally refers to converting at least large hydrocarbon molecules to smaller hydrocarbon molecules by breaking at least one carbon-carbon bond (see, e.g., U.S. Pat. No. 5,770,043). The long chains of carbon in the alkenones produced by algae (e.g., 35-40 carbons) can be used to produce a wider range of biofuels or lubricating oils than those derived from glycerides (e.g., 14 to 22 carbons).

In certain embodiments, the subject methods comprise converting algal alkenones into a liquid fuel such as diesel or gasoline. In other embodiments, the subject methods comprise converting algal alkenones into a gaseous fuel, such as a syngas (a mixture of CO and $H_2$) and/or a synthetic hydrocarbon gas (e.g., methane, propane, and butane).

In certain specific embodiments, the subject methods comprise converting the long chains of the alkenones into methane and supercritical carbon dioxide by technologies that use high temperature liquid metal chemistry. Such technologies are known in the art (see e.g., the technologies developed by Quantum Catalytics; http://www.txsyn.com/org_quantum.html). For example, algal biomass may be converted into methane via hydrothermal gasification (see, e.g., Haiduc et al., J. Appl. Phycol., 2009, 21:529-541; and Stucki et al., Energy Environ. Sci., 2009, 2:535-541). Optionally, growing of algae and hydrothermal processing of biomass may be coupled into a continuous process. It may be possible to introduce the algal biomass directly into a reactor for hydrothermal gasification. Thus, this approach may allow the use of the algae cells, directly without first extracting the algae oil, for the production of hydrocarbons or polymers, eliminating several costly steps such as solvent extraction.

Conversion of Algal Lipids to Polymers

In some embodiments, the algal lipids of the present application have use as feedstock in the industrial chemical field, particularly in the manufacture of polymers. In certain embodiments, the algal lipids can be polymerized, either directly or after some chemical modification. In other embodiments, the algal lipids can be pyrolyzed or cracked into smaller molecules to permit the generation of standard monomers, such as acrylic acids and esters, alkenes (ethene, propene, etc.), vinyl chloride, vinyl acetate, diacids, diamines, diols, lactic acid, etc.

EXEMPLIFICATION

The invention now being generally described, it will be more readily understood by reference to the following examples, which are included merely for purposes of illustration of certain aspects and embodiments of the present invention, and are not intended to limit the invention.

Introduction

In preparation for a future 1-acre-sized bioproduction site in Cape Cod, Mass., USA (41° 33 05"N, −70° 36 55"W), we surveyed local species capable of sustainable growth and high production of FAMEs in the low incidence of annual light availability and cool temperatures of the region. One of our targeted algae was the coastal marine prymnesiophyte *Isochrysis* sp. including strains T-Iso and C-Iso (FIG. 1). We were interested in *Isochrysis* sp. as they are rich in polyunsaturated fatty acids (PUFAs), can be grown both indoors and outdoors (D. Kaplan et al., CRC Press, FL, 1986, pp. 147-198), have no cell walls, and are grown commercially for mariculture feedstocks (P. Lavens and P. Sorgeloos, Manual on the production and use of live food for aquaculture, Fisheries Technical Paper 361, Food and Agriculture Organization of the United Nations, 1996; M. Albentosa, et al. Aquaculture, 1996, 148, 11-23; C. T. Enright, et al., Journal of Experimental Marine Biology and Ecology, 1986, 96, 1-13). Furthermore, this effort conforms with the future fuels strategy proposed by Inderwaldi and King stressing the importance of in-depth scientific analysis of short, medium, and long-term aspects of biofuel production (O. R. Inderwildi and D. A. King, *Energy & Environmental Science*, 2009, 2, 343-346).

Methods and Materials

1. Microalgal Species and Culture Conditions

Two *Isochrysis* sp. strains "T-Iso" and "C-Iso" and the diatom, *Thalassiosira weissflogii* strain "TW" were sourced from the Milford Laboratory Microalgal Culture Collection (Milford, Conn.). Additional information on the "T-Iso" and "C-Iso" strains have been described in detail (G. H. Wikfors and G. W. Patterson, *Aquaculture,* 1994, 123, 127-135). In this study, we included TW to highlight differences in lipid profiles of algae. Microalgae were cultured in 250-ml glass Erlenmeyer flasks under 24-hour lighting (approximately 31 $\mu mol \cdot photons\ m^{-2}\ s^{-1}$.) and held on an oscillating shaker (100 rpm) at 19° C. Standard f/2 media was used for cultures with silica provided for the comparison "TW" strain. Microalgae were harvested by centrifuging at 4,000 rpm and decanting the supernatant. The remaining algal pellet was freeze-dried.

2. Extraction of Algal Samples

Freeze-dried algal biomass (10 to 50 mg) were extracted with hexane. The resultant lipid extract was spiked with an internal standard, ethyl nonadecanoate, and transesterified under $N_2$ using 10% methanolic HCl in hexane (55° C.; 12 hours). We used ethyl nonadecanoate to check both the completeness of the transesterification reaction by monitoring the production of methyl nonadecanoate and using the latter for quantification purposes. The reaction products were extracted with hexane, reduced in volume, spiked with an external standard, n-heptadecane, and stored until analysis by the GC-FID.

3. Analysis by Gas Chromatography with Flame Ionization Detection (GC-FID)

We quantified FAMEs and alkenones in the esterified samples using a Hewlett-Packard 5890 GC-FID. Compounds were separated on a glass capillary column (J&W DB-1MS, 30 m, 0.25-mm i.d., 0.25-µm film thickness) with $H_2$ carrier gas. FAMEs were identified with standards purchased from Nu-Chek Prep (Elysian, Minn.) and Supelco (Bellefonte, Pa.). Alkenones were identified based on comparison to published elution order on gas chromatographic columns, their mass spectra, and mixtures harvested from cultures of *Isochrysis* sp. Methyl nonadecanoate recoveries were always >90%. No ethyl nonadecanoate was observed in the samples.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of producing alkenone derivatives from an algal extract, the method comprising:
    (a) culturing a large surface growth area of alkenone-producing algae under a growth condition sufficient to produce alkenones within the algae;

(b) drying the algae and extracting lipids and alkenones from the algae to produce an alkenone-containing extract;

(c) chemically modifying the alkenones in the alkenone-containing extract of step (b) to produce alkenone derivatives, wherein the alkenone derivatives comprise hydrocarbons, polymers, or combinations thereof; and (d) recovering the alkenone derivatives from the extract after step (c).

2. The method of claim 1, wherein the alkenone-producing algae is a species of the Isochrysis family.

3. The method of claim 2, wherein the alkenone-producing algae is selected from: *Isochrysis galbana, Isochrysis* sp. T-Iso, and *Isochrysis* sp. C-Iso.

4. The method of claim 1, wherein the alkenones comprise a number of carbons ranging from 35 to 40.

5. The method of claim 1, wherein the chemically modifying step (c) comprises pyrolyzing, or catalytic hydroprocessing of the alkenones.

6. The method of claim 1, wherein the alkenone derivatives of step (c) are acrylic acids, acrylic esters, alkenes, vinyl chloride, vinyl acetate, diacids, diamines, diols, or lactic acid.

7. The method of claim 1, wherein the alkenone derivatives of step (c) are hydrocarbons.

8. The method of claim 7, wherein the alkenones are converted into hydrocarbons by catalytic hydroprocessing.

9. The method of claim 1, wherein the growth condition includes a stationary growth phase.

10. The method of claim 1, wherein the growth condition includes sufficient light.

11. The method of claim 1, wherein the growth condition includes nutrient limitation.

12. The method of claim 1, wherein the alkenone derivatives are recovered from the extract at step (d) using an enzyme, a structured enzyme array or system, a viral agent, a solvent, supercritical fluid extraction or a combination thereof.

13. The method of claim 12, wherein the alkenone derivatives are recovered from the extract using an enzyme, a structured enzyme array or system or a combination thereof.

14. The method of claim 12, wherein the alkenone derivatives are recovered from the extract using a hexane or butane solvent.

15. The method of claim 1, further comprising the step of polymerizing the alkenone derivatives.

16. The method of claim 1, wherein the alkenone-producing algae are grown in one or more of a reservoir structure, pond, trough, tube, raceway pond, or bioreactor.

* * * * *